US009829478B2

(12) United States Patent
Maikap et al.

(10) Patent No.: US 9,829,478 B2
(45) Date of Patent: Nov. 28, 2017

(54) DETECTION MODULE AND METHOD FOR OPERATING THE SAME

(71) Applicant: CHANG GUNG UNIVERSITY, Taoyuan (TW)

(72) Inventors: Siddheswar Maikap, Taoyuan (TW); Pankaj Kumar, Taoyuan County (TW)

(73) Assignee: Chang Gung University, Taoyuan (TW)

( * ) Notice: Subject to any disclaimer, the term of this patent is extended or adjusted under 35 U.S.C. 154(b) by 157 days.

(21) Appl. No.: 14/833,237

(22) Filed: Aug. 24, 2015

(65) Prior Publication Data
US 2017/0059504 A1    Mar. 2, 2017

(51) Int. Cl.
*G01N 27/333* (2006.01)
*G01N 33/49* (2006.01)
*C12Q 1/26* (2006.01)
*G01N 27/00* (2006.01)

(52) U.S. Cl.
CPC .............. *G01N 33/49* (2013.01); *C12Q 1/26* (2013.01); *G01N 27/00* (2013.01); *G01N 2333/90638* (2013.01)

(58) Field of Classification Search
CPC ........................... G01N 27/301; G01N 27/333
See application file for complete search history.

(56) References Cited

U.S. PATENT DOCUMENTS

| 5,480,534 A * | 1/1996 | Kato ................... G01N 27/333 204/192.1 |
| 2010/0038243 A1* | 2/2010 | White ................ G01N 27/333 204/416 |

FOREIGN PATENT DOCUMENTS

WO      WO 2014052962 A1 *   4/2014   ............... C12Q 1/26

OTHER PUBLICATIONS

S. Negi, et al. "Effect of sputtering pressure on pulsed-DC sputtered iridium oxide film" Sensors and Actuators B: Chemical, vol. 137, No. 1, Mar. 2009, p. 370-378.*
P. Kumar, et al., "Time-dependent pH sensing phenomena using CdSe/ZnS quantum dots in EIS structure", Nanoscale Research Letters, vol. 9, No. 1, Apr. 2014, paper No. 179, 7 pgs.*
H.B. Campbell, et al., "Towards a reliable and high sensitivity O2-independent glucose sensor based on Ir oxide particles" Biosensors and Bioelectronics, vol. 42, Apr. 2013, p. 563-569.*

* cited by examiner

*Primary Examiner* — J. Christopher Ball
(74) *Attorney, Agent, or Firm* — Rosenberg, Klein & Lee

(57) ABSTRACT

A detection module and a method for operating the same are revealed. A nano-scale iridium oxide membrane is used as a detection film. After being in contact with different concentrations of hydrogen peroxide, the iridium oxide membrane is oxidized or reduced to generate iridium (III) ions ($Ir^{3+}$) or iridium (IV) ions ($Ir^{4+}$). Thus a voltage shift is generated. Whether hydrogen peroxide is contained in the sample can be checked by detection of changes in the voltage. A sample is formed by mixing serum and benzylamine. When the serum in the sample contains LOXL2 enzyme associated with breast cancer, the LOXL2 enzyme reacts with benzylamine to get hydrogen peroxide which is used as a detection medium.

9 Claims, 5 Drawing Sheets

DETECTION MODULE AND METHOD FOR OPERATING THE SAME

FIELD OF THE INVENTION

The present invention relates to a detection module and a method for operating the same, especially to a detection module and a method for operating the same for rapid screening of breast cancer.

BACKGROUND OF THE INVENTION

Breast cancer is the most common cancer among women, occurring mostly in regions with high economic performance, especially North America, Northern Europe, Western Europe, Central Europe, etc. Nowadays the incidence of breast cancer is increasing due to changes in living environment and eating habits. Thus early-stage diagnosis and treatment of breast cancer have become an important public health issue.

Breast cancer screening test available now includes mammography. By using low-energy X-rays, abnormalities in the breast in the form of the smallest to less than 5 mm (zero stage) and calcium spots can be detected and breast cancer at zero stage without symptoms is found out. Yet the mammography has its limitations. About 15 percent of breast cancer goes undetected by mammography. The test cost is high and bulky test equipment is required. Thus people are unable to perform exams at home. Another test method is breast ultrasound. It is much better to monitor the breast tumor through ultrasound; however, the heavy test equipment is still required and thus people are unable to do tests at home.

Breast cancer staging means looking at the tumor size and whether the tumor has spread to the nearby lymph nodes or other parts of the body. If the breast cancer is detected at early stages, breast conserving surgery is an option and 5-year survival rate is up to 90%. Once the detection method can be simplified, the early-stage breast cancer can be found out easier, and the survival rate of the patients with breast cancer can be further increased.

Now scientists have found that Lysyl oxidase homolog 2 (Lysyl oxidase-like 2, LOXL2) enzyme is associated with invasiveness and metastasis in breast cancer. It has also found that blocking the LOXL2 enzyme significantly slowed the spread of breast cancer. The researchers inhibited the activity of the LOXL2 gene in mice with breast cancer. Thus the spread of tumor cells to distant areas in the body is effectively prevented. Thereby new drugs that inhibit LOXL2 enzyme have been developed to treat breast cancer. In the field of cancer detection, whether LOXL2-related mechanism can be applied to simplify a flow chart of breast cancer detection also has become a hot issue.

SUMMARY

Therefore it is a primary object of the present invention to provide a detection module that checks whether a sample contains hydrogen peroxide according to changes in voltage. The detection of changes in voltage is based on iridium (III) ions ($Ir^{3+}$) or iridium (IV) ions ($Ir^{4+}$) generated by oxidation and reduction of iridium oxide in contact with different concentrations of hydrogen peroxide.

It is another object of the present invention to provide a detection module that detects a sample formed by mixing of serum and benzylamine. If the serum contains LOXL2 enzyme therein, LOXL2 enzyme reacts with benzylamine to get hydrogen peroxide. The hydrogen peroxide further reacts with iridium-oxide.

It is a further object of the present invention to provide a detection module that has a high sensitivity to LOXL2 (Lysyl oxidase homolog 2) enzyme. Once serum in a sample contains traces of LOXL2, a detectable change in the charge as well as voltage is generated instantly. LOXL2 in the serum is one of the biomarkers of breast cancer. Thus the detection module of the present invention can be used for breast cancer detection.

It is a further object of the present invention to provide a detection module that has simple structure. The detection module can be used in the form of a commercial chip for breast cancer detection. Thus the breast cancer detection is more convenient and the detection results can be learned instantly.

It is a further object of the present invention to provide a method for operating a detection module that compares the voltage of an iridium oxide membrane before and after the contact with a sample so as to get a voltage shift and further check whether a serum in the sample contains LOXL2 or not.

In order to achieve the above objects, a detection module of the present invention includes a conductive substrate, an electrically conductive layer disposed over the conductive substrate, an iridium oxide membrane arranged over the electrically conductive layer and used for loading a sample, and a reference electrode located at the iridium oxide membrane and used for contact with the sample.

In order to achieve the above objects, a method for operating a detection module according to the present invention includes the following steps. First, use a reference electrode to close with an iridium oxide membrane and get a first voltage. Then, dispose a sample between the reference electrode and the iridium oxide membrane to get a second voltage. The sample is a mixture of serum and benzylamine. Next, compare the first voltage with the second voltage to get a difference. Once the difference is not zero, the serum in the sample contains LOXL2 enzyme.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION

In order to learn features and functions of the present invention, please refer the following embodiments and detailed description.

Figure 1:
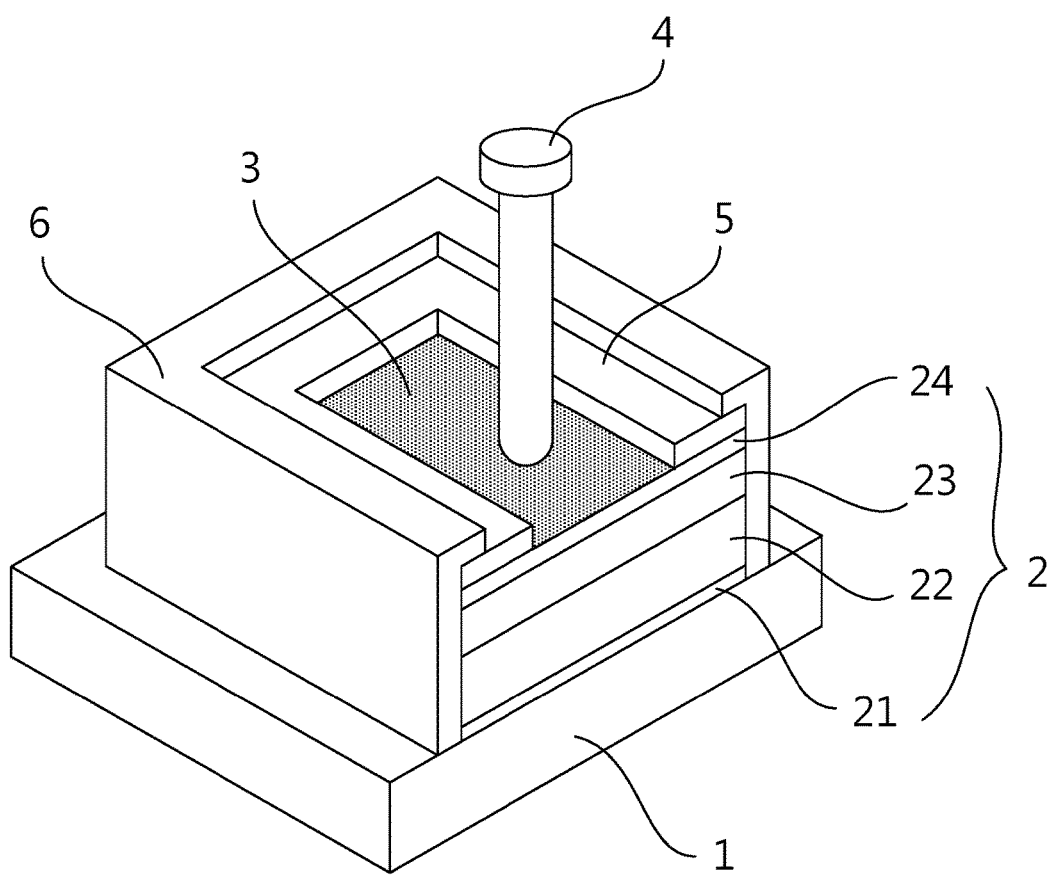
FIG. 1 is schematic drawing showing a cross section of an embodiment according to the present invention.

Refer to FIG. 1, a detection module of the present invention includes a conductive substrate 1, a conductive substrate 1, an electrically conductive layer 2, an iridium oxide membrane 3, and a reference electrode 4. The electrically conductive layer 2 is disposed over the conductive substrate 1 and the iridium oxide membrane 3 is arranged over the electrically conductive layer 2 while the reference electrode 4 is located at the iridium oxide membrane 3.

In a preferred embodiment, the conductive substrate 1 is a copper-plated printed circuit board and is used as an electrode tip in relation to the reference electrode 4 in the detection module. As to the electrically conductive layer 2 over the conductive substrate 1, it includes a silver paste layer 21, an aluminum layer 22, a silicon layer 23, and a silicon oxide layer 24 stacked in turn. The silicon oxide layer 24 is partially covered by the iridium oxide membrane 3. There is no limit on the formation ways of the respective layer in the electrically conductive layer 2. The respective layer can be formed by various ways such as chemical vapor deposition (CVD), plasma-enhanced chemical vapor deposition (PECVD), evaporation, electron beam evaporation, radio frequency magnetron sputtering, etc. Thus the layers made from different materials respectively are stacked in turn. The reference electrode 4 can be a silver-silver chloride electrode or other reference electrode with a fixed potential difference.

Figure 2A:
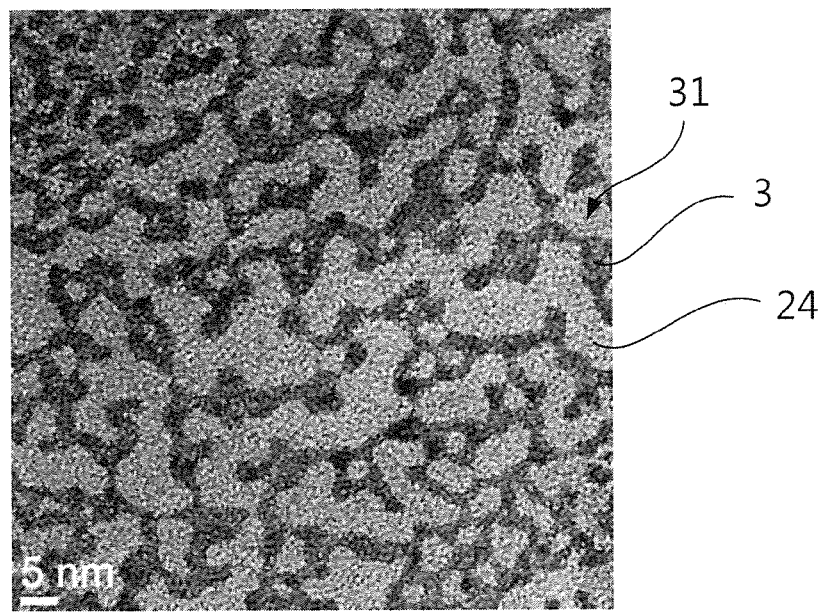
FIG. 2A is a partial enlarged view of an embodiment showing an iridium oxide membrane coated over a silicon oxide layer according to the present invention.
Figure 2B:
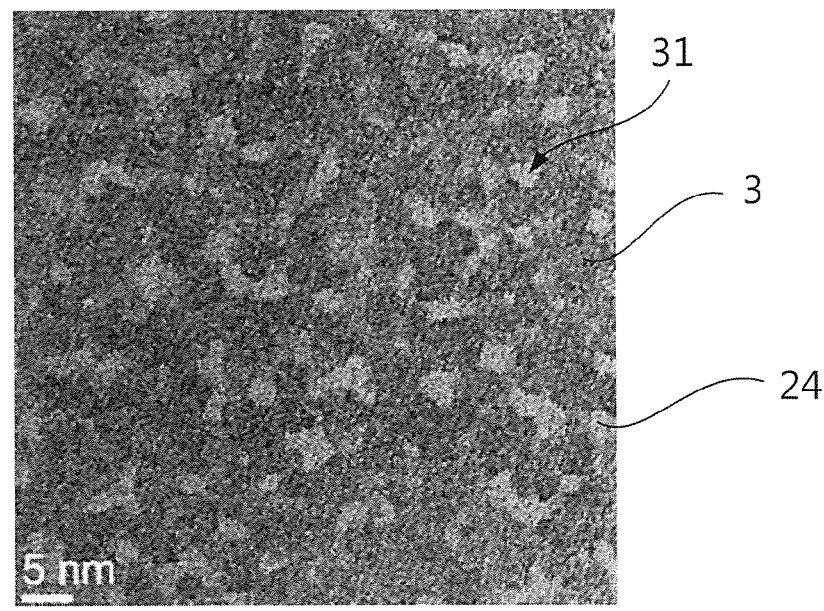
FIG. 2B is a partial enlarged view of an embodiment showing an iridium oxide membrane coated over a silicon oxide layer according to the present invention.

Refer to FIG. 2A and FIG. 2B, in these two preferred embodiments, the iridium oxide membrane 3 is not completely coated on the silicon oxide layer 24 in the form of a thick film or membrane. The iridium oxide ($IrO_x$) is scattered over the silicon oxide layer 24 in the form of nanoparticles. The thickness of the membrane is ranging from 1 nanometer to 2 nanometers. The thickness of the embodiment in FIG. 2A is thinner than the thickness of the embodiment in FIG. 2B. Moreover, the iridium oxide membrane 3 includes a plurality of vacant portions 31 where the electrically conductive layer 2 there under is exposed. In these preferred embodiments, the structure of the electrically conductive layer 2 exposed is the uppermost silicon oxide layer 24.

Back to FIG. 1, while in use, a liquid sample is dropped on surface of the iridium oxide membrane 3. In order to prevent the excessive sample from flowing freely, there is at least one resin block 5 is further disposed over the electrically conductive layer 2. A distinct detection space is formed on the electrically conductive layer 2 by the resin block 5. The iridium oxide membrane 3 mentioned above is located over the electrically conductive layer 2 and within the detection space. The material for the resin block 5 can be SU-8 that is a commonly used negative photoresist. The SU-8 is first spin-coated and then baked to form the resin block 5 with the distinctive detection space used in the present invention.

Furthermore, the detection module of the present invention may further includes a housing 6 formed by epoxy resin and used for preventing the electrically conductive layer 2 therein from being contaminated or oxidized. Thus the service life of the detection module is extended.

While in use, the liquid sample is dropped on surface of the iridium oxide membrane 3. In a preferred embodiment, the sample is a mixture of serum and benzylamine. It is known that LOXL2 enzyme is closely associated with metastasis and mortality in breast cancer. When tumor cells grow and proliferate for a period of time, they start to breach multiple barriers in organisms and escape from the circulatory system for finding out new ways. At the moment, the tumor cells secret a lot amount of LOXL2 enzyme for accelerating degradation of defense system of the basement membrane and the extracellular matrix, and allowing the tumor cells spread out. Thus if there is any LOXL2 enzyme found in the sample, the patients with breast cancer can be screened due to abnormal secretion of LOXL2 enzyme from breast cancer cells.

The sample used in the present invention includes not only serum. The serum is firstly mixed with benzylamine and then the following reaction-reaction 1 is carried out.

$$LOXL2 + C_6H_5CH_2NH_2 \rightarrow H_2O_2 \quad \text{(reaction 1)}$$

The LOXL2 in the serum reacts with benzylamine to get hydrogen peroxide. That means if there is hydrogen peroxide in the sample, there is LOXL2 in the serum. In the present invention, the sample is in contact with the iridium oxide membrane and then the following reactions including reaction 2 and/or reaction 3 are carrier out.

$$H_2O_2 + IrO_x \rightarrow Ir^{3+} + 2H^+ + 2O_2 \quad \text{(reaction 2)}$$

$$Ir^{3+} + H_2O_2 + 2H^+ \rightarrow Ir^{4+} + 2H_2O \quad \text{(reaction 3)}$$

In the reaction 2, an inorganic oxide is reduced by peroxide to get inorganic ion $Ir^{3+}$. Hydrogen peroxide is used as reductant and the product is oxygen. Refer to the reaction 3, $Ir^{3+}$ ion is further oxidized into $Ir^{4+}$ ion by the hydrogen peroxide in an acidic environment and the product is water. After the sample used in the present invention being in contact with the iridium oxide membrane, not only the reaction 2 and reaction 3 mentioned above occur. More oxidation or reduction reactions may occur according to different concentration of hydrogen peroxide. The amount of the $Ir^{3+}$ and $Ir^{4+}$ is not limited, as long as there is a certain amount of iridium ions generated.

Figure 3:
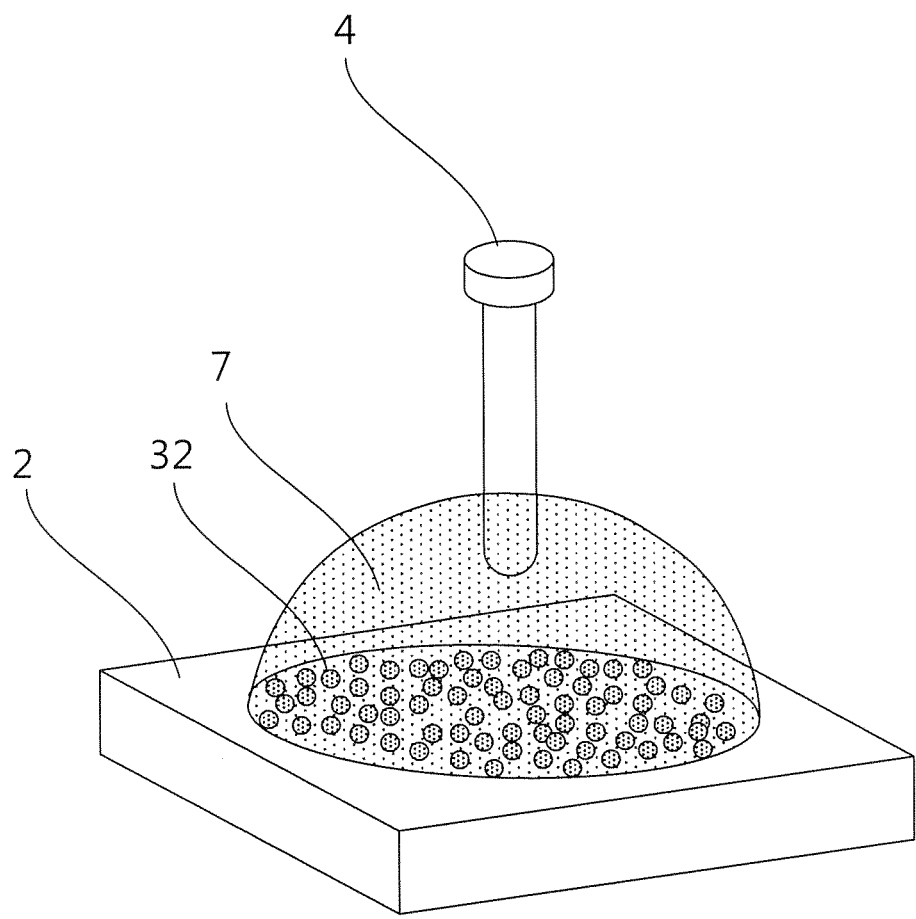
FIG. 3 is a schematic drawing showing a sample dropped on an iridium oxide membrane and in contact with both the iridium oxide membrane and a reference electrode in an embodiment according to the present invention.

The iridium ions generated are in the sample. Refer to FIG. 3, the reference electrode 4 is in contact with the sample 7. In a pathway that communicates the reference electrode 4, the sample 7, the iridium oxide membrane 3, the electrically conductive layer 2 and the conductive substrate 1, iridium ions 32 are generated due to oxidation and/or reduction reaction between iridium oxide nanoparticles in the iridium oxide membrane 3 and hydrogen peroxide. Thus detectable change in voltage is further generated. Therefore whether the serum contains LOXL2 enzyme or not can be detected sensitively and instantly for evaluating the risk of cancers.

Figure 4:
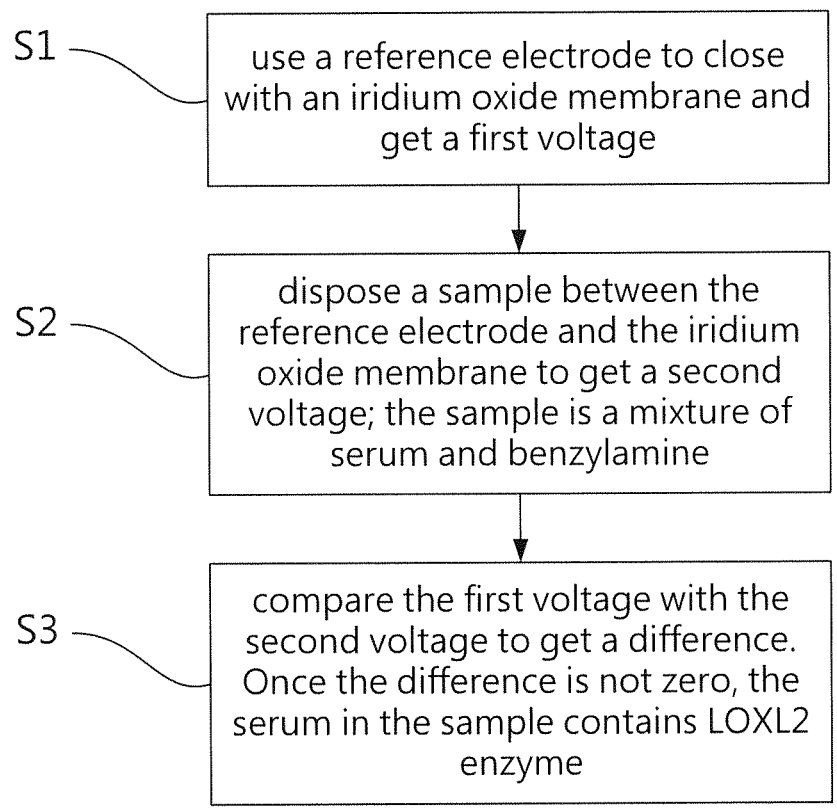
FIG. 4 is a flow chart showing steps of an embodiment according to the present invention.

Refer to FIG. 4, a method for operating a detection module of the present invention includes the following steps.

Step S1: use a reference electrode to close with an iridium oxide membrane and get a first voltage;

Step S2: dispose a sample between the reference electrode and the iridium oxide membrane to get a second voltage; the sample is a mixture of serum and benzylamine; and Step S3: compare the first voltage with the second voltage to get a difference. Once the difference is not zero, the serum in the sample contains LOXL2 enzyme.

Figure 5:
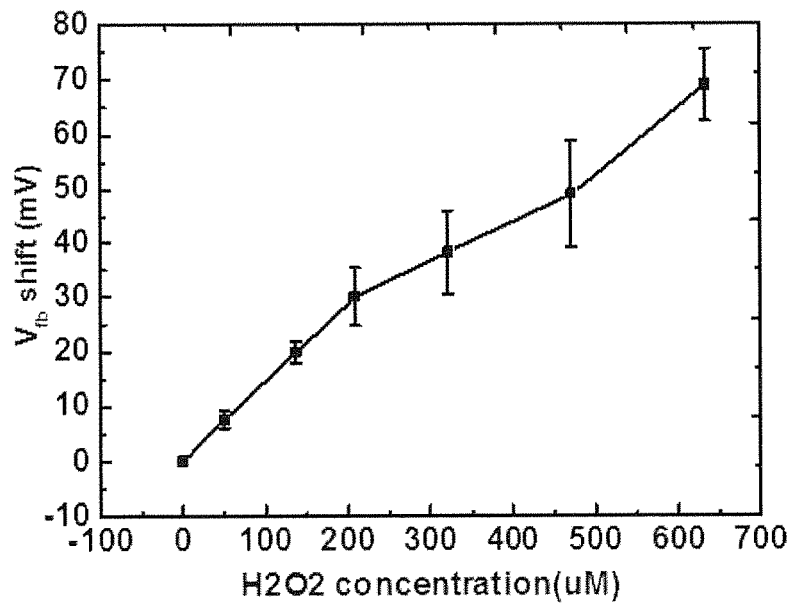
FIG. 5 is a curve showing the relationship between hydrogen peroxide concentration and voltage shift in an embodiment according to the present invention.

Refer to FIG. 5, a curve that shows the effect of different concentrations of hydrogen oxide on the change in voltage detected by the detection module is revealed. As shown in the figure, even there is only a trace amount of hydrogen oxide (low concentration), the voltage shift is detectable. Thus the detection module of the present invention has high sensitivity.

Figure 6:
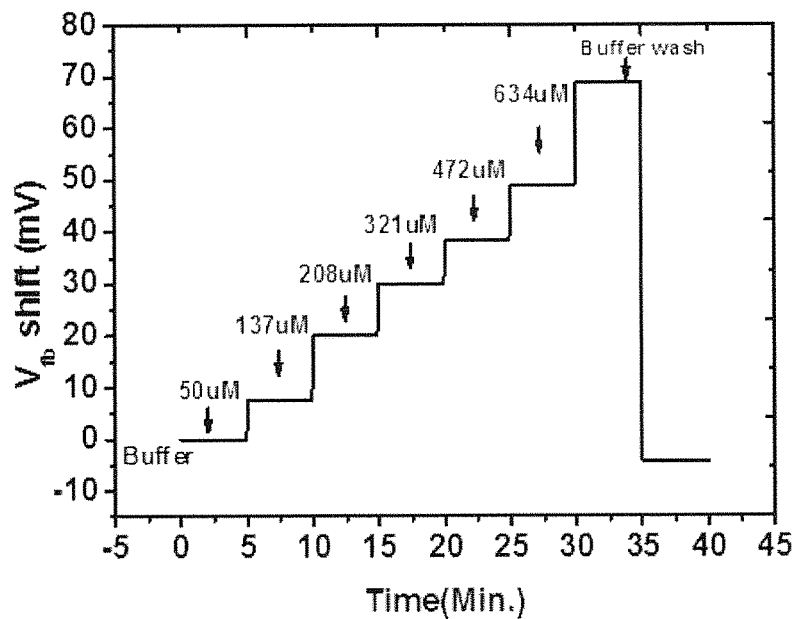
FIG. 6 is a curve showing the relationship between voltage shift and reaction time of LOXL2 enzyme and benzylamine in an embodiment according to the present invention.

Refer to FIG. 6, the concentration of the hydrogen peroxide is increased over time. That means more LOXL2 enzyme has been reacted with benzylamine and more hydrogen peroxide is further produced.

In addition, a buffer solution is added between the iridium oxide membrane and the reference electrode. The buffer solution is used to change the pH value of the sample and further adjust substrate bias.

In summary, the present invention provides a detection module and a method for operating the same. The sample detected by the detection module is a mixture of serum and benzylamine. If the serum contains LOXL2 enzyme associated with breast cancer, LOXL2 enzyme reacts with benzylamine to get hydrogen peroxide. The detection module of the present invention uses the iridium oxide in contact with different concentrations of hydrogen peroxide to get iridium (III) ions ($Ir^{3+}$) or iridium (IV) ions ($Ir^{4+}$) due to oxidation or reduction. Then whether the sample contains hydrogen peroxide is checked by detection of changes in voltage. The detection features on rapid detection and high sensitivity. Thus the detection module and the method for operating the same of the present invention are of great value in developing detection kit for breast cancer.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

The invention claimed is:

1. A detection module comprising:
   a conductive substrate;
   an electrically conductive layer disposed over the conductive substrate;
   an iridium oxide membrane arranged over the electrically conductive layer and used for loading a sample; and
   a reference electrode located at the iridium oxide membrane and used for contact with the sample.

2. The detection module as claimed in claim 1, wherein the conductive substrate is a copper-plated printed circuit board.

3. The detection module as claimed in claim 1, wherein the electrically conductive layer includes:
   a silver paste layer disposed over the conductive substrate;
   an aluminum layer arranged over the silver paste layer;
   a silicon layer set over the aluminum layer; and
   a silicon oxide layer disposed over the silicon layer and partially covered by the iridium oxide membrane.

4. The detection module as claimed in claim 1, wherein a thickness of the iridium oxide membrane is ranging from 1 nanometer to 2 nanometers.

5. The detection module as claimed in claim 1, wherein the iridium oxide membrane includes a plurality of vacant portions where the electrically conductive layer thereunder is exposed.

6. The detection module as claimed in claim 1, wherein a buffer solution is added between the iridium oxide membrane and the reference electrode.

7. The detection module as claimed in claim 1, wherein at least one resin block is disposed over the electrically conductive layer and a detection space is formed by the resin block; the iridium oxide membrane is located over the electrically conductive layer and within the detection space.

8. The detection module as claimed in claim 1, wherein the sample is a mixture of serum and benzylamine.

9. A method for operating a detection module as claimed in claim 1 comprising the steps of:
   using a reference electrode to close with an iridium oxide membrane and get a first voltage;
   disposing a sample between the reference electrode and the iridium oxide membrane to get a second voltage while the sampling having serum and benzylamine;
   comparing the first voltage with the second voltage to get a difference; if the difference is not zero, the serum in the sample contains LOXL2 enzyme.

* * * * *